(12) United States Patent
Takekoshi et al.

(10) Patent No.: US 7,572,057 B2
(45) Date of Patent: Aug. 11, 2009

(54) RADIOGRAPHY CONTROL APPARATUS AND RADIOGRAPHY CONTROL METHOD

(75) Inventors: Koji Takekoshi, Yokohama (JP);
Tsukasa Sako, Yokohama (JP); Toshio Kameshima, Kumagaya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/143,058

(22) Filed: Jun. 20, 2008

(65) Prior Publication Data

US 2008/0317215 A1  Dec. 25, 2008

(30) Foreign Application Priority Data

Jun. 21, 2007  (JP) .............................. 2007-163352
Jun. 21, 2007  (JP) .............................. 2007-163353

(51) Int. Cl.
*A61B 6/08* (2006.01)

(52) U.S. Cl. .................................................. 378/205

(58) Field of Classification Search ......... 378/193–198, 378/205, 114–117; 250/370.08, 370.09
See application file for complete search history.

(56) References Cited

U.S. PATENT DOCUMENTS 7,401,977 B2 * 7/2008 Graumann et al. .......... 378/205

2007/0223657 A1 * 9/2007 Birdwell ...................... 378/205
2008/0112541 A1 * 5/2008 Hardesty ..................... 378/205

FOREIGN PATENT DOCUMENTS

| JP | 5-064081 A | 3/1993 |
| JP | 3066944 B | 5/2000 |
| JP | 2004-73354 A | 3/2004 |
| JP | 3624106 B | 12/2004 |

OTHER PUBLICATIONS

JIS handbook 2005, T0601-1-3, Japanese Standards Association, Medical Electrical Equipment, Part 1: General Requirements for Safety—3. Collateral Standard: General Requirements for Radiation Protection in Diagnostic X-ray Equipment, pp. 562-581.

* cited by examiner

*Primary Examiner*—Courtney Thomas
(74) *Attorney, Agent, or Firm*—Canon U.S.A., Inc., IP Division

(57) ABSTRACT

A control device controls a radiography apparatus including a radiation generating unit that emits radiation, a radiation detecting unit that detects the radiation emitted from the radiation generating unit. The control device includes a positional-relationship detecting unit that detects a positional relationship between the radiation generating unit and the radiation detecting unit when the radiography apparatus performs a radiographic operation; and a control unit that controls the radiographic operation of the radiography apparatus based on the result of the detection performed by the positional-relationship detecting unit.

11 Claims, 14 Drawing Sheets

RADIOGRAPHY CONTROL APPARATUS AND RADIOGRAPHY CONTROL METHOD

BACKGROUND OF THE INVENTION

1. Field of the Invention

The present invention relates to a radiography control apparatus and a radiography control method for capturing a radiographic image.

2. Description of the Related Art

Film-screen systems using an intensifying screen and an X-ray film in combination are often used as X-ray machines in hospitals. In this type of system, X-rays pass through an object and are converted into visible light having an intensity proportional to that of the X-rays by the intensifying screen. The X-ray film is exposed to the visible light, and thus an X-ray image can be obtained. The film is observed using an observing apparatus called a viewing box.

Japanese Patent Laid-Open No. 05-064081 discusses an X-ray television apparatus which performs a radioscopic operation in which an X-ray radioscopic image is displayed on a cathode-ray tube (CRT) monitor using an image intensifier. Such an apparatus has come into widespread use in medical applications.

Japanese Patent No. 3066944 discusses a high resolution solid-state X-ray detecting device using a flat panel detector (FPD). In this device, an object is placed between an X-ray source and an X-ray detector. The intensity of X-rays that pass through the object is converted into electrical signals. Thus, digital data representing an X-ray image of the object can be obtained.

Japanese Patent Laid-Open No. 2004-73354 discusses a cassette-type sensor capable of capturing an image using a portable sensor unit has been put to practical use. Japan Industrial Standard (JIS) specifies the degree of coincidence between an X-ray irradiation area and an image-receiving area for X-ray radioscopy using cassette-type sensors (JIS handbook 2005, radiation, T0601-1-3, medical electrical equipment, Japanese Standards Association".

Japanese Patent No. 3624106 describes a method for easily determining an image-capturing position by emitting electromagnetic waves from an X-ray generating device toward the flat panel detector.

FIG. 24 is a schematic diagram illustrating the relationship between an X-ray flat panel detector and an X-ray irradiation area. In X-ray radioscopy using a cassette-type flat panel detector 1, the flat panel detector 1 is disposed at a predetermined position and an object is placed on the flat panel detector 1 to capture an X-ray image of the object.

The relationship between an irradiation area T of X-rays emitted from an X-ray tube and the flat panel detector 1 is specified as follows. A displacement between the boundaries of the X-ray irradiation area T and the corresponding boundaries of the flat panel detector 1 along two orthogonal main axes of the flat panel detector 1 must be no more than 3% of the distance between the focal point of the X-ray tube and the flat panel detector 1. In addition, the total displacement along the two axes must be no more than 4% of the distance between the focal point of the X-ray tube and an X-ray sensor 13.

The flat panel detector 1 and the X-ray irradiation area T are required to satisfy the following conditions:

$|x1|+|x2| \leq 0.03 \cdot D$ $|y1|+|y2| \leq 0.03 \cdot D$ $|x1|+|x2|+|y1|+|y2| \leq 0.04 \cdot D$ where $x1$ and $x2$ are displacements between the boundaries of the flat panel detector 1 and the X-ray irradiation area T along the main axis Ax of the flat panel detector 1, $y1$ and $y2$ are displacements between the boundaries of the flat panel detector 1 and the X-ray irradiation area T along the main axis Ay of the flat panel detector 1, and D is the distance between the focal point of the X-ray tube and the flat panel detector 1.

According to Japanese Patent No. 3624106, while the position of the flat panel detector 1 can be detected, the X-ray radiographic operation cannot be controlled. This results in an area outside the flat panel detector being irradiated with X-rays.

Also in the invention according to Japanese Patent Laid-Open No. 2004-73354, the X-ray radiographic operation cannot be controlled. In addition, the positional relationship between the X-ray source and the flat panel detector is not taken into account, and X-rays are emitted in the radioscopic operation even when the positional relationship is such that the area outside the flat panel detector can be irradiated with the X-rays.

Even if the positional relationship is such that all of the X-rays are incident on the flat panel detector, there is a risk that the positional relationship will change such that some of the X-rays leak instead of being incident on the flat panel detector for some reason. Also in such a case, the X-rays are continuously emitted in the radioscopic operation.

SUMMARY OF THE INVENTION

The present invention is directed to a radiography apparatus and a radiography method for controlling a radiographic operation based on the positional relationship between a radiation source and a flat panel detector.

According to an aspect of the present invention, a control device controls a radiography apparatus including a radiation generating unit that emits radiation, a radiation detecting unit that detects the radiation emitted from the radiation generating unit. The control device includes a positional-relationship detecting unit that detects a radiant positional relationship between the radiation generating unit and the radiation detecting unit when the radiography apparatus performs a radiographic operation; and a control unit that controls the radiographic operation of the radiography apparatus based on the result of the detection performed by the positional-relationship detecting unit.

Other features of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Exemplary embodiments of the present invention will be described in detail in accordance with the accompanying drawings.

First Exemplary Embodiment

Figure 1:
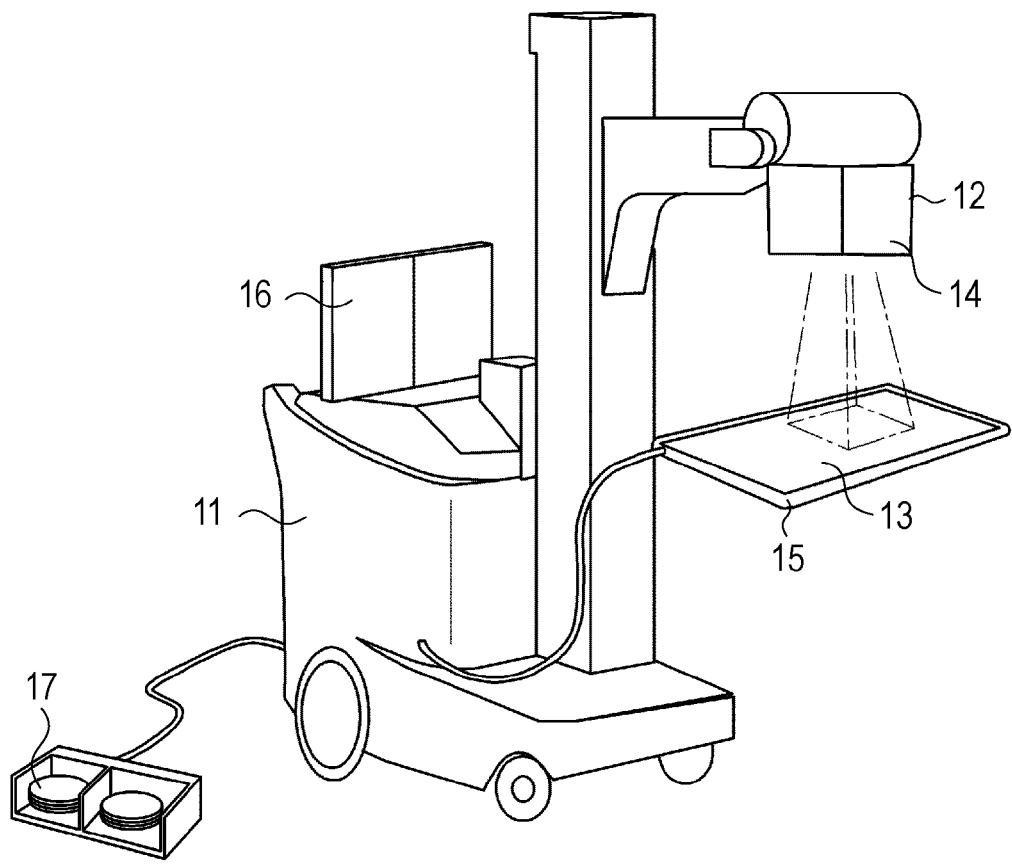
FIG. 1 is a system diagram illustrating an X-ray radiography apparatus according to a first embodiment.

FIG. 1 is a system diagram illustrating the structure of an X-ray radiography apparatus mounted on an instrument carriage 11 according to a first exemplary embodiment. The instrument carriage 11 is movable, and has an X-ray generating unit 12 and an X-ray sensor 13 mounted thereon. The X-ray sensor 13 is connected to a control unit (not shown) disposed in the instrument carriage 11.

The X-ray generating unit 12 includes an X-ray tube that emits X-rays, an X-ray stop, and a movement detection sensor 14. The X-ray sensor 13 receives X-rays emitted by the X-ray generating unit 12 and thereby obtains image signals. The X-ray sensor 13 includes a movement detection sensor 15. The X-ray generating unit 12 has a single electromagnetic-wave transmitting device, and the X-ray sensor 13 has at least three electromagnetic-wave receiving devices.

The instrument carriage 11 has a display unit 16 for displaying an image captured by the X-ray sensor 13. The display unit 16 includes a general monitor, such as a CRT monitor and a liquid crystal display, and displays image data, a graphical user interface (GUI), etc. on a screen. A foot pedal 17 is disposed outside the instrument carriage 11. The foot pedal 17 is used to issue an instruction to start or stop the emission of the X-rays and is connected to the control unit with a cable.

The X-ray radiography apparatus also includes a general input device (not shown) including, for example, a keyboard, a mouse, etc., in addition to the foot pedal 17, so that a user can input commands through the input device.

Figure 2:
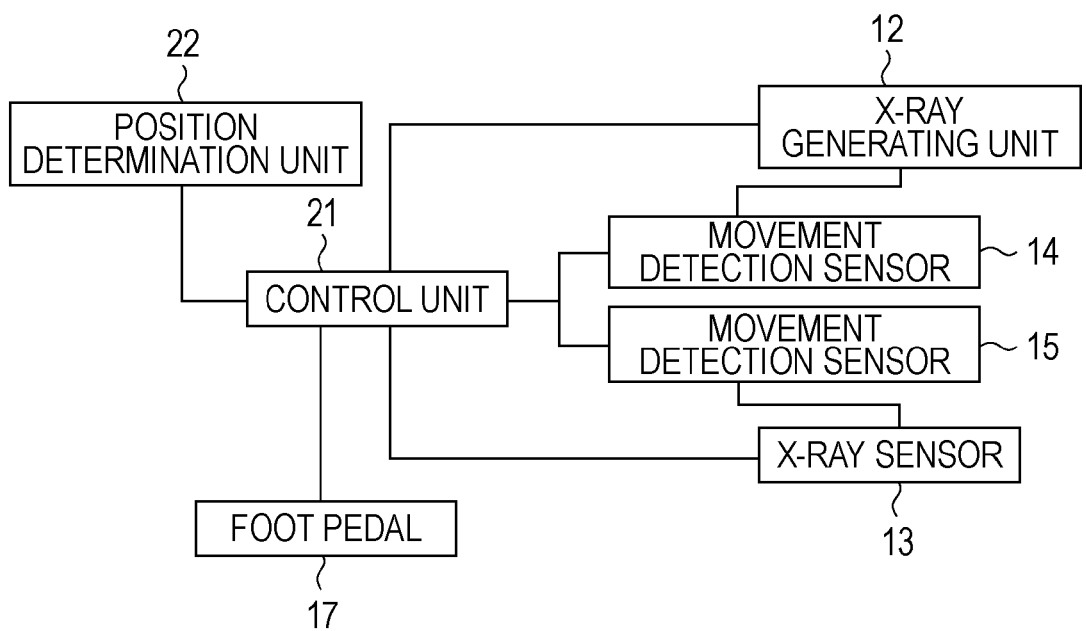
FIG. 2 is a block circuit diagram illustrating the structure of the first embodiment.

FIG. 2 is a block circuit diagram of the X-ray radiography apparatus. A control unit 21 is connected to the X-ray generating unit 12, the X-ray sensor 13, the movement detection sensors 14 and 15, the foot pedal 17, and a position determining unit 22. The control unit 21 performs various control operations for the X-ray generating unit 12 and the X-ray sensor 13, and is disposed in the instrument carriage 11 together with the position determining unit 22.

The control unit 21 and the position determining unit 22 are provided as functions obtained by causing a central processing unit (CPU) (not shown) to execute programs. The CPU may include an LSI or an ASIC.

Figure 3:
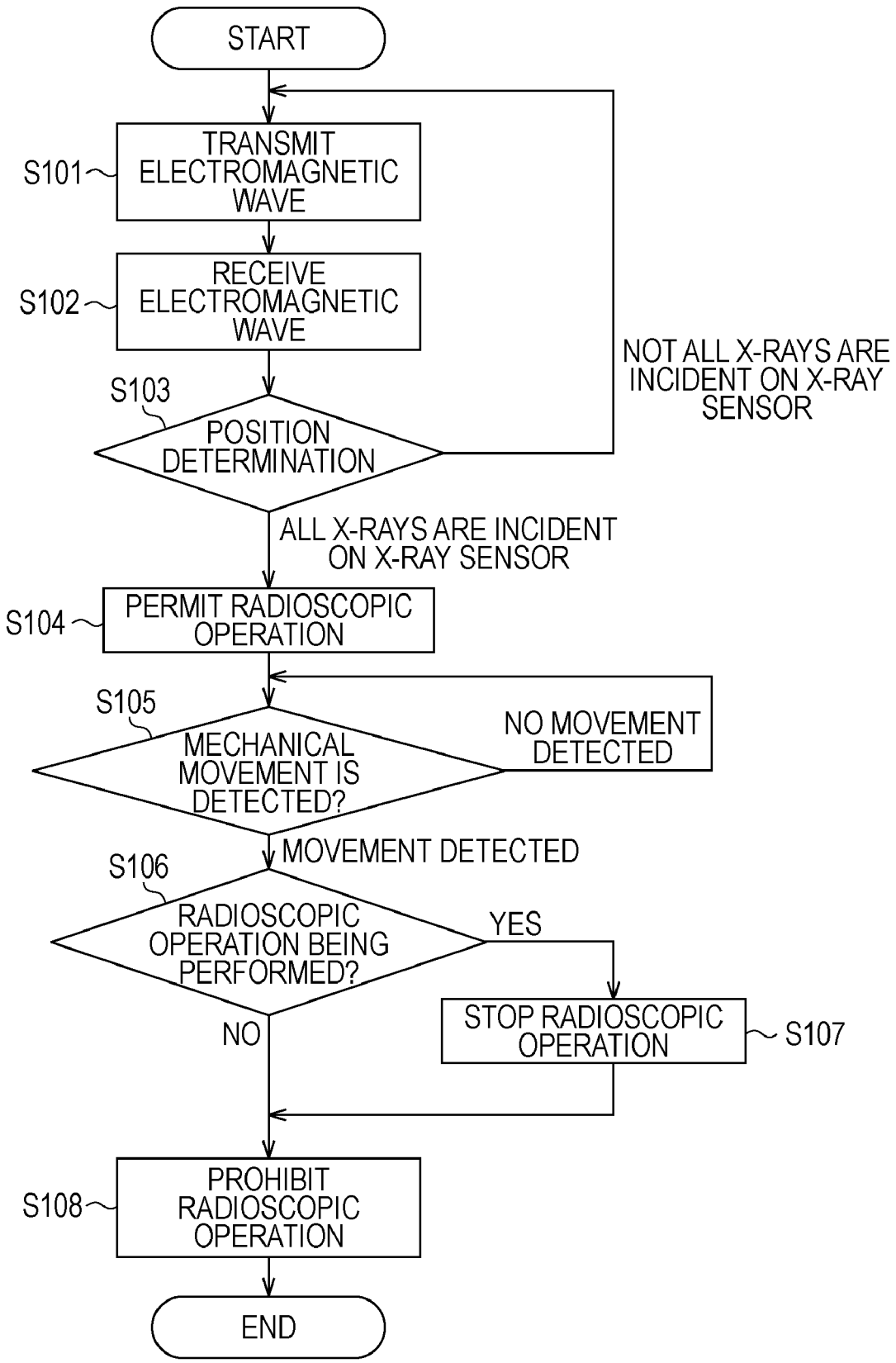
FIG. 3 is a flowchart of the operation according to the first embodiment.
Figure 4A:
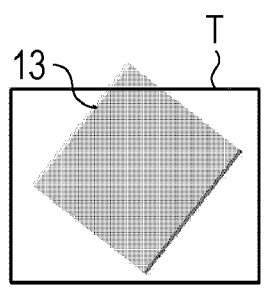
FIGS. 4A to 4L illustrate the relationships between an X-ray sensor and an X-ray irradiation area according to the first embodiment.
Figure 4B:
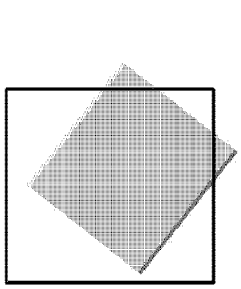
Figure 4C:
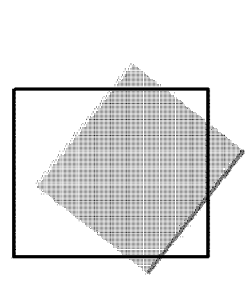
Figure 4D:
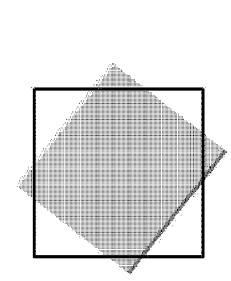
Figure 4E:
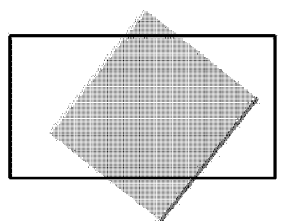
Figure 4F:
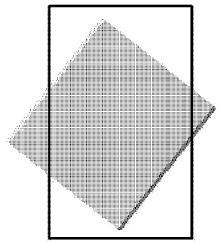
Figure 4G:
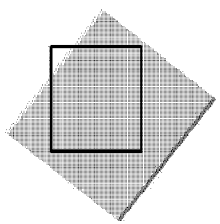
Figure 4H:
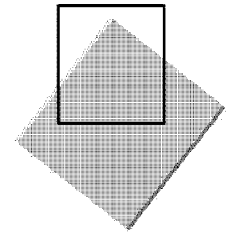
Figure 4I:
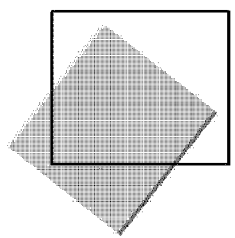
Figure 4J:
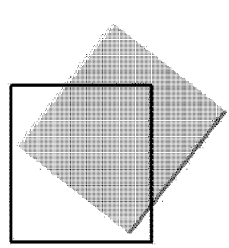
Figure 4K:
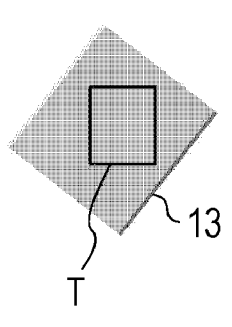
Figure 4L:
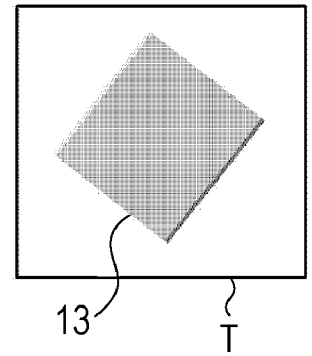

FIG. 3 is a flowchart of the operation according to the present embodiment. First, in step S101, an electromagnetic wave is emitted from the electromagnetic-wave transmitting device provided on the X-ray generating unit 12. Then, in step S102, the electromagnetic wave is received by the electromagnetic-wave receiving devices provided on the X-ray sensor 13. Three or more electromagnetic-wave receiving devices are provided. The distance between the focal point of the X-ray generating unit 12 and the X-ray sensor 13 is determined on the basis of the delay times of the times at which the electromagnetic wave emitted from the electromagnetic-wave transmitting device is received. The number of electromagnetic-wave transmitting devices is not limited to one, and two or more electromagnetic-wave transmitting devices may also be provided.

Next, in step S103, the position determining unit 22 performs a position determination process. In this process, it is determined whether or not the X-ray generating unit 12 and the X-ray sensor 13 are in an opposed relationship on the basis of the delay times of the times at which the electromagnetic wave transmitted in step S101 is received in step S102. The opposed relationship refers to the state in which all of the X-rays emitted from the X-ray generating unit 12 are incident on the X-ray sensor 13.

The above-described opposed relationship is established when an X-ray irradiation area T is positioned inside the X-ray sensor 13. For example, FIGS. 4A to 4L show patterns of positional relationships between the X-ray sensor 13 and the X-ray irradiation area T. In the pattern shown FIG. 4K, the X-ray generating unit 12 and the X-ray sensor 13 are in the opposed relationship and the X-ray irradiation area T is disposed inside the X-ray sensor 13.

As an exception, it may be determined that the X-ray generating unit 12 and the X-ray sensor 13 are in the opposed relationship when the X-ray irradiation area T has a rectangular shape and three vertices thereof are disposed inside the X-ray sensor 13. The X-ray source is similar to a point source, and therefore the emitted X-rays diverge as the distance from the source is increased. Thus, if the distance between the X-ray generating unit 12 and the X-ray sensor 13 is too large, there may be a case in which the X-ray irradiation area T is not disposed inside the X-ray sensor 13 due to the divergence of the X-rays.

Figure 5:
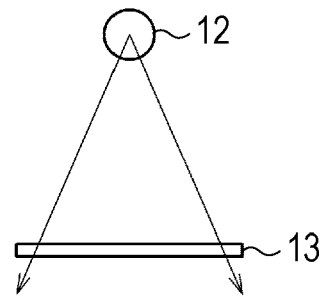
FIG. 5 illustrates the state in which the X-ray irradiation area is disposed inside the X-ray sensor according to the first embodiment.
Figure 6:
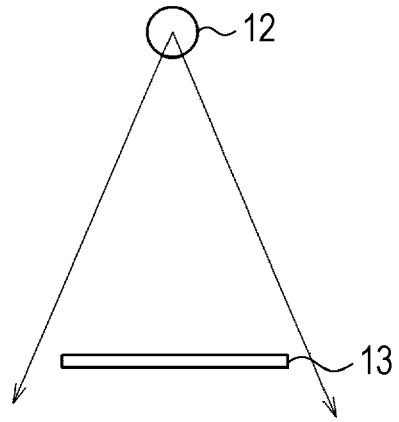
FIG. 6 illustrates the state in which the X-ray irradiation area is not disposed inside the X-ray sensor according to the first embodiment.

In FIG. 5, the X-ray generating unit 12 and the X-ray sensor 13 are relatively close to each other, so that the X-ray irradiation area T is disposed inside the X-ray sensor 13. In comparison, in FIG. 6, the distance between the X-ray generating unit 12 and the X-ray sensor 13 is larger than that in FIG. 5. Therefore, the X-ray irradiation area T protrudes from the X-ray sensor 13. The X-ray generating unit 12 and the X-ray sensor 13 are in the opposed relationship in FIG. 5, but are not in the opposed relationship in FIG. 6.

Figure 7:
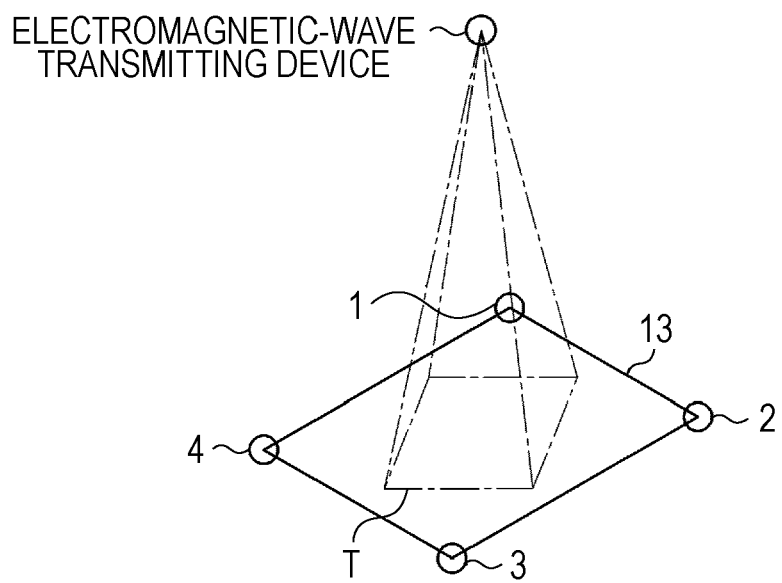
FIG. 7 is a conceptual diagram of an electromagnetic-wave transmitting device and electromagnetic-wave receiving devices according to the first embodiment.

Referring to FIG. 7, electromagnetic-wave receiving devices 1 to 4 are attached to a surface of the X-ray sensor 13 at predetermined positions. The spatial positional relationship between the X-ray generating unit 12 and the X-ray sensor 13 can be uniquely determined by estimating the distances between the electromagnetic-wave transmitting device and the electromagnetic-wave receiving devices 1 to 4. Since the propagation velocity of the electromagnetic wave is determined in advance, the distance between the X-ray generating unit 12 and the X-ray sensor 13 can be estimated on the basis of the differences between the transmission time and the reception times of the electromagnetic wave.

Figure 8:
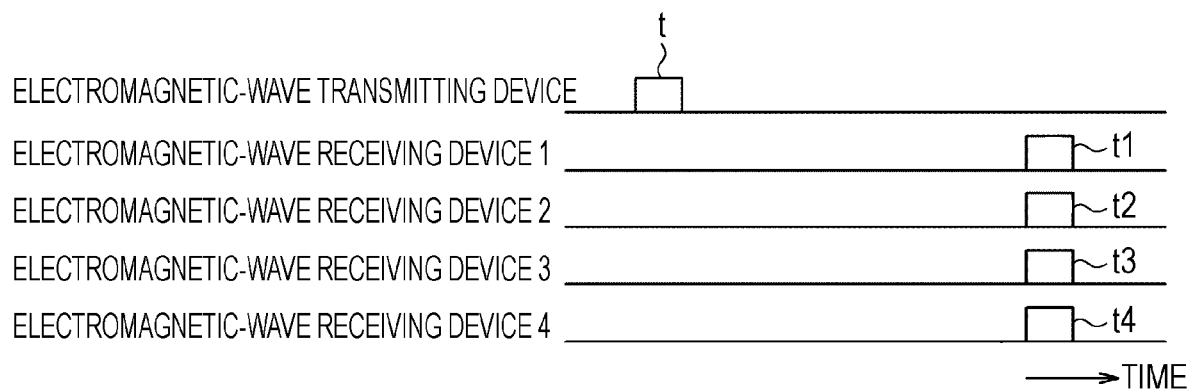
FIG. 8 is a timing chart illustrating the times at which an electromagnetic wave is emitted and received according to the first embodiment.

Referring to FIG. 8, the electromagnetic wave is transmitted from the electromagnetic-wave transmitting device at time t, and is received by the electromagnetic-wave receiving devices 1 to 4 at times t1, t2, t3, and t4, respectively. If the reception times t1 to t4 are equal to each other, the main axis of the X-ray generating unit 12 and that of the X-ray sensor 13 coincide with each other.

Figure 9:
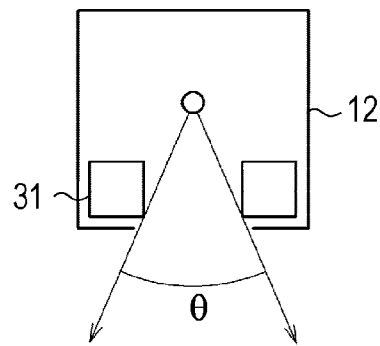
FIG. 9 is a schematic diagram of an X-ray emitting unit according to the first embodiment.

FIG. 9 is a schematic diagram of the X-ray generating unit 12. An emission angle θ of the X-ray generating unit 12 is generally determined by an aperture. More specifically, an X-ray stop 31 having an adjustable aperture is disposed on the emission side of the X-ray generating unit 12, and the irradiation area of the X-rays can be freely changed by adjusting the aperture. Although the target angle of the X-rays and the shape of the X-ray irradiation area T vary in accordance with the adjustment of the X-ray stop 31, the shape can be determined on the basis of the aperture in the X-ray stop 31. The shape of the X-ray irradiation area T is not limited to rectangular, and may also be hexagonal, octagonal, etc., depending on the shape of the X-ray stop 31.

As described above, the spatial positional relationship between the X-ray generating unit 12 and the X-ray sensor 13 is uniquely determined on the basis of the times at which the electromagnetic wave is transmitted and received. Therefore, whether or not the opposed relationship is established can be determined by estimating the emission angle of the X-rays on the basis of the X-ray stop information and estimating whether or not all of the X-rays emitted from the X-ray generating unit 12 are incident on the X-ray sensor 13.

Next, in step S104 shown in FIG. 3, an X-ray radioscopic operation is permitted if it is determined by the position determining unit 22 that the opposed relationship is established in step S103. The process of permitting the radioscopic operation can be performed by automatically setting a radioscopic mode or by setting a state in which the radioscopic mode can be set. At this time, the X-ray generating unit 12 and the X-ray sensor 13 may be locked to prevent the X-ray generating unit 12 and the X-ray sensor 13 from moving. The radioscopic mode refers to an image-capturing method for continuously performing an image-capturing operation instead of capturing a single still image, and includes cinematography for saving images and digital subtraction angiography (DSA).

Next, in step S105, it is determined whether or not a mechanical movement is detected. The detection of the mechanical movement is performed by the movement detection sensor 14 attached to the X-ray generating unit 12 and the movement detection sensor 15 attached to the X-ray sensor 13. An opening or closing operation of the X-ray stop 31 included in the X-ray generating unit 12 is detected as a movement. A method for detecting the movement of a movable body described in Japanese Patent Laid-Open No. 2004-73354 may also be applied.

Inertial sensors are used as the movement detection sensors 14 and 15. However, other known sensors, such as angle sensors, velocity sensors, linear sensors, etc., may also be used. These sensors are used for detecting the movement, and a plurality of sensors may be used. A plurality of kinds of sensors, of course, may be used in combination.

If it is determined that a mechanical movement has occurred on the basis of the detection results obtained by the movement detection sensors 14 and 15 in the state in which the radioscopic operation is permitted, the process proceeds to step S106. In step S106, it is determined whether or not the radioscopic operation is being performed. If the radioscopic operation is being performed, the radioscopic operation is stopped in step S107. More specifically, the control unit 21 may be operated so as to stop the emission of X-rays immediately. Alternatively, the emission of X-rays may be stopped after a predetermined time period. After the radioscopic operation is stopped, step S108 is executed. Step S108 is executed also when it is determined that the radioscopic operation is not performed in step S106.

In step S108, the radioscopic operation is prohibited. The process of prohibiting the radioscopic operation is performed by, for example, disabling the selection of the radioscopic mode by the user through the GUI. Alternatively, the control unit 21 may be operated such that the radioscopic operation is not performed even when a request for the radioscopic operation is input to the control unit 21 from the outside. Alternatively, the power may be turned off.

Second Embodiment

Figure 10:
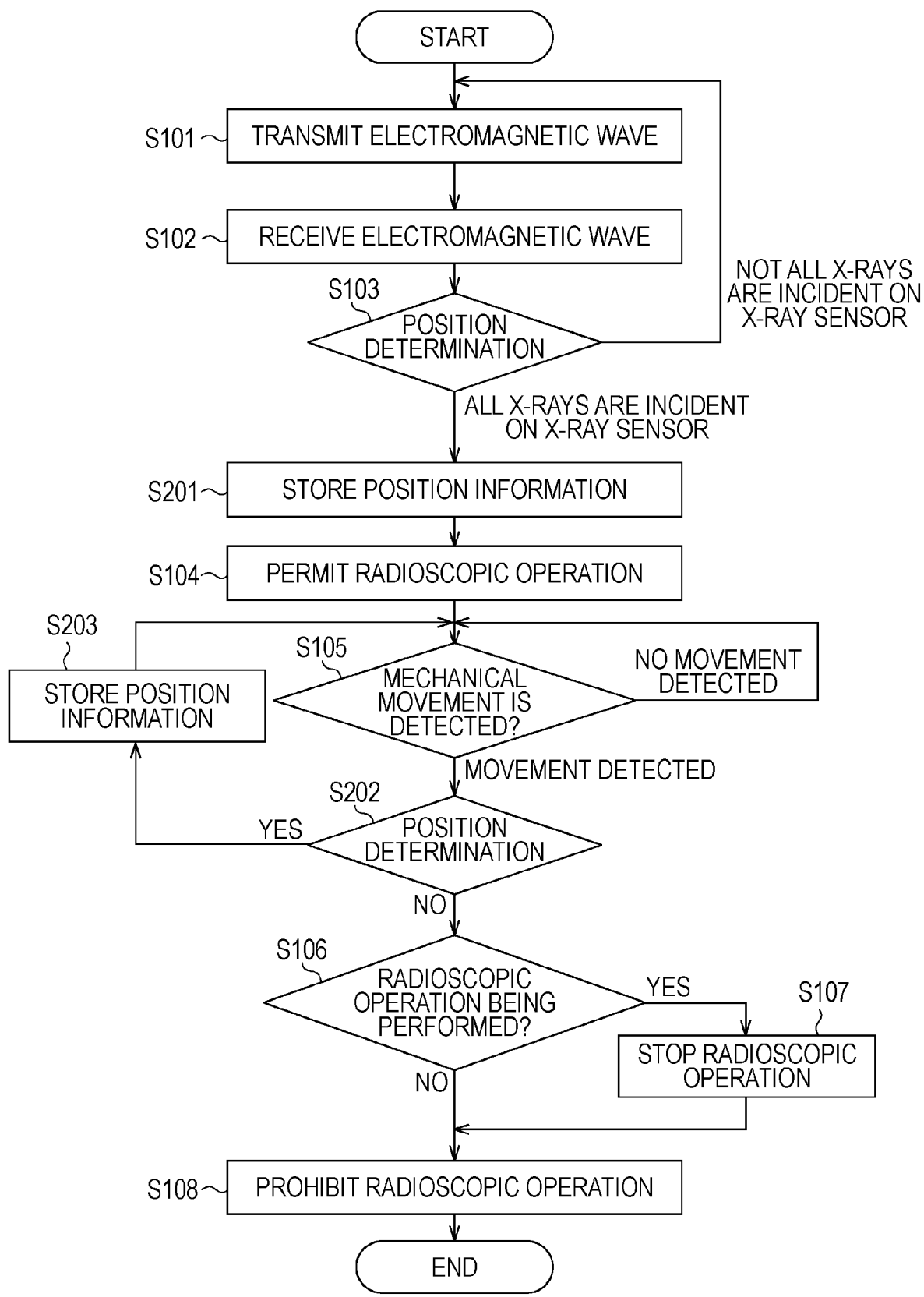
FIG. 10 is a flowchart of the operation according to a second embodiment.

FIG. 10 is a flowchart of the operation according to a second embodiment. In FIG. 10, steps similar to those of the first embodiment shown in FIG. 3 are denoted by the same step numbers. In the first embodiment, the radioscopic operation is stopped immediately or after a predetermined time period if a mechanical movement is detected in step S105.

In the second embodiment, steps S101 to S103 are similar to those of the first embodiment. In step S201, the X-ray irradiation area T is stored as position information based on the target angle of the X-ray irradiation, the position of the X-ray stop, the distance between the X-ray focus point and the X-ray sensor 13, and the positions thereof. For example, the region where the X-ray irradiation area T is positioned with respect to the X-ray sensor 13 is stored.

Then, step S104 is executed. Then, if a mechanical movement is detected in step S105, a displacement of the X-ray irradiation area T is estimated on the basis of the information obtained from the movement detection sensors 14 and 15. In step S202, it is determined whether or not the opposed relationship is established on the basis of the result of the estimation and the position information stored in step S201. For example, since the X-ray irradiation area T on the X-ray sensor 13 is estimated in advance, the new X-ray irradiation area T on the X-ray sensor 13 can be determined by obtaining the amount of relative movement between the X-ray generating unit 12 and the X-ray sensor 13. As a result, it can be determined whether or not the opposed relationship is established.

If it is determined that the X-ray irradiation area T remains inside the X-ray sensor 13 after the mechanical movement, the position information after the mechanical movement is stored in step S203. Then, the process proceeds to step S105 while the radioscopic operation is continuously permitted. If the X-ray irradiation area T is not disposed inside the X-ray sensor 13 after the mechanical movement, the process proceeds to step S106.

Third Embodiment

Figure 11:
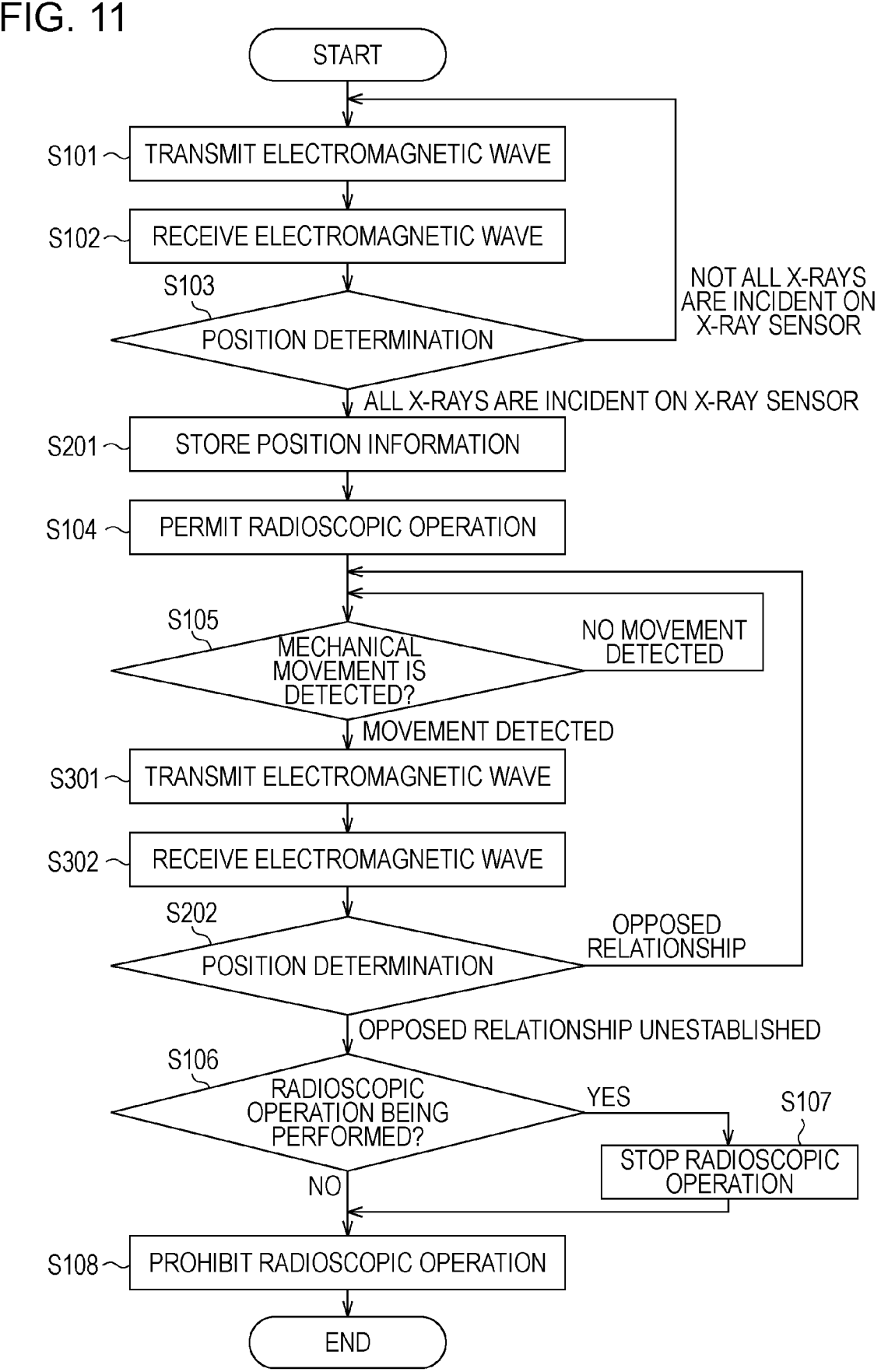
FIG. 11 is a flowchart of the operation according to a third embodiment.

FIG. 11 is a flowchart of the operation according to a third embodiment. In FIG. 11, steps similar to those of the first and second embodiments are denoted by the same step numbers. In the second embodiment, the position information obtained in the position determination process performed in step S103 is stored in step S201. Then, if a mechanical movement is detected in step S105, it is determined whether or not the opposed relationship is established on the basis of the position information and the amount of mechanical movement.

In the present embodiment, if a mechanical movement is detected, the electromagnetic wave is transmitted again in step S301, and the thus transmitted electromagnetic wave is received in step S302. Then, the position determination process similar to that performed in step S103 is performed.

According to the flowchart shown in FIG. 11, the transmission and reception of the electromagnetic wave are performed before the position determination process. However, the transmission and reception of the electromagnetic wave for the position determination process may also be performed continuously.

Fourth Embodiment

Figure 12:
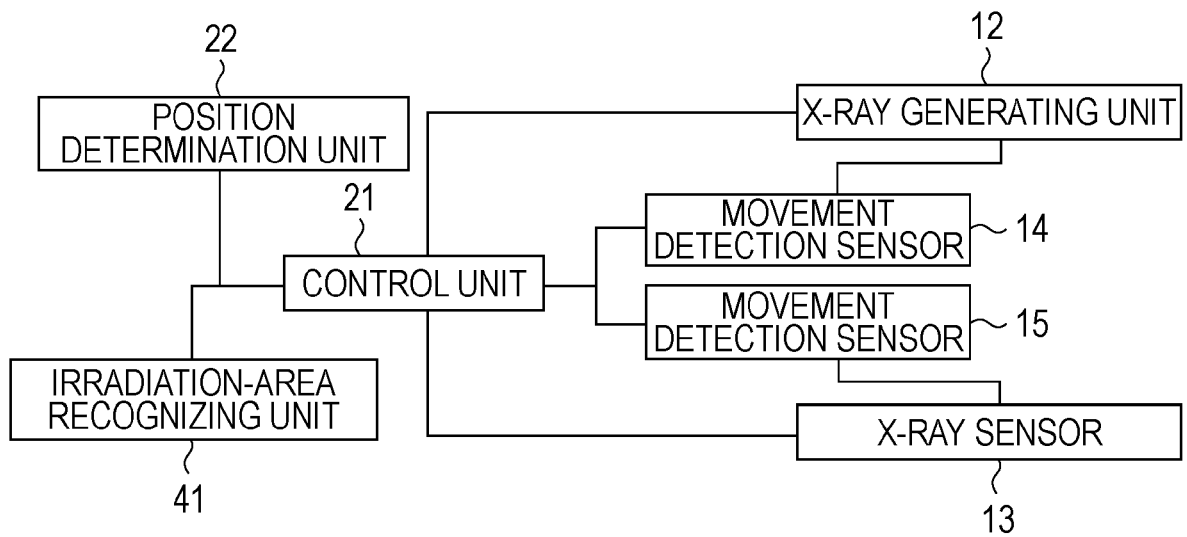
FIG. 12 is a system diagram illustrating an X-ray radiography apparatus according to a fourth embodiment.

FIG. 12 is a block circuit diagram according to a fourth embodiment. FIG. 12 differs from FIG. 2 in that an irradiation-area recognizing unit 41 is connected to the control unit 21.

Figure 13:
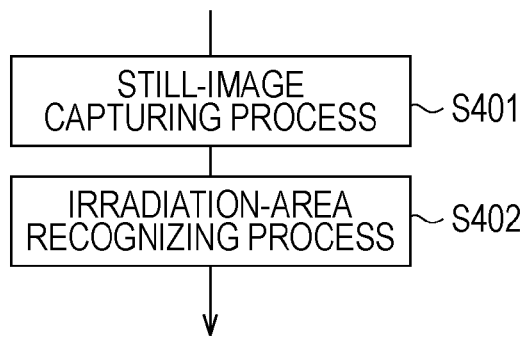
FIG. 13 is a flowchart of the operation according to the fourth embodiment.

According to the present embodiment, the position determination process is performed in step S103 after transmitting the electromagnetic wave in step S101 and receiving the electromagnetic wave in step S102. FIG. 13 is a flowchart of this operation. A still image is captured in step S401, and an irradiation area is recognized in step S402.

In the process of capturing a still image performed in step S401, the control unit 21 causes the X-ray generating unit 12 to emit the X-rays and the X-ray sensor 13 to receive the thus emitted X-rays, so that an image can be captured. In step S402, the process of recognizing the irradiation area is performed by the irradiation-area recognizing unit 41. More specifically, the X-ray irradiation area T on the X-ray sensor 13 is determined by performing a known image analyzing process. Thus, the X-ray irradiation area T on the X-ray sensor 13 can be determined by performing the process of recognizing the irradiation area.

Next, in step S103, the position determination process is performed on the basis of the recognition result of the irradiation area obtained in step S402. More specifically, it is determined that the X-ray irradiation area T is disposed inside the X-ray sensor 13 if none of the peripheral sides of the X-ray irradiation area T intersect any of the peripheral sides of the X-ray sensor 13.

Figure 14:
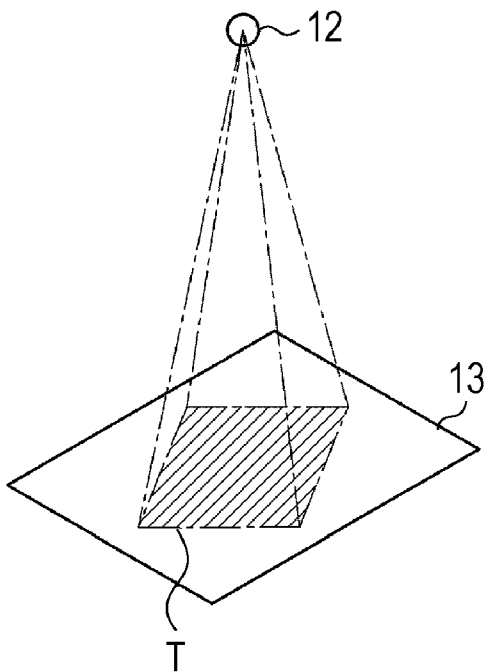
FIG. 14 illustrates the state in which an X-ray irradiation area is disposed inside an X-ray sensor according to the fourth embodiment.

FIG. 14 shows the case in which the X-ray irradiation area T is disposed inside the X-ray sensor 13. None of the peripheral sides of the X-ray irradiation area T intersects any of the peripheral sides of the X-ray sensor 13. If no X-ray is incident on the X-ray sensor 13, the irradiation area cannot be recognized by the irradiation-area recognizing unit 41 and an error is issued.

If any of the peripheral sides of the X-ray irradiation area T intersect any of the peripheral sides of the X-ray sensor 13, it is determined that the X-ray irradiation area T is not disposed inside the area of the X-ray sensor 13.

Figure 15:
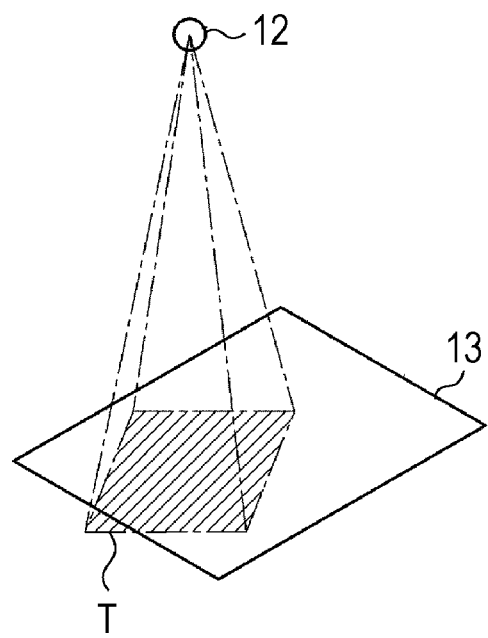
FIG. 15 illustrates the state in which the X-ray irradiation area is not disposed inside the X-ray sensor according to the fourth embodiment.

FIG. 15 shows the case in which the X-ray irradiation area T is not disposed inside the X-ray sensor 13. The X-ray sensor 13 and the X-ray irradiation area T overlap each other, and one of the peripheral sides of the X-ray sensor 13 intersects the peripheral sides of the X-ray irradiation area T.

As another method for the position determination process, it may be determined that the X-ray irradiation area T is disposed inside the X-ray sensor 13 if none of the peripheral sides of the X-ray irradiation area T extracted in step S402 coincides with any of the peripheral sides of the X-ray sensor 13. If any of the peripheral sides of the X-ray irradiation area T coincide with any of the peripheral sides of the X-ray sensor 13, it is determined that the X-ray irradiation area T is not disposed inside the X-ray sensor 13.

If it is determined that the X-ray irradiation area T is disposed inside the X-ray sensor 13 as a result of the position determination process, the process similar to step S104 in the first to third embodiments is performed. If the X-ray irradiation area T protrudes from the X-ray sensor 13, the system returns to the initial state.

The still image captured in the fourth embodiment is a single image, and the captured image is not particularly limited as long as the irradiation area can be recognized. Therefore, the conditions of the X-rays may either be set to those for a normal operation for capturing a still image or to those for the radioscopic operation.

The method according to the embodiments of the present invention may be stored in a storage medium, such as a disc, a floppy disk, etc., in the form of a program that can be supplied to the X-ray radiography apparatus.

Fifth Embodiment

Figure 16:
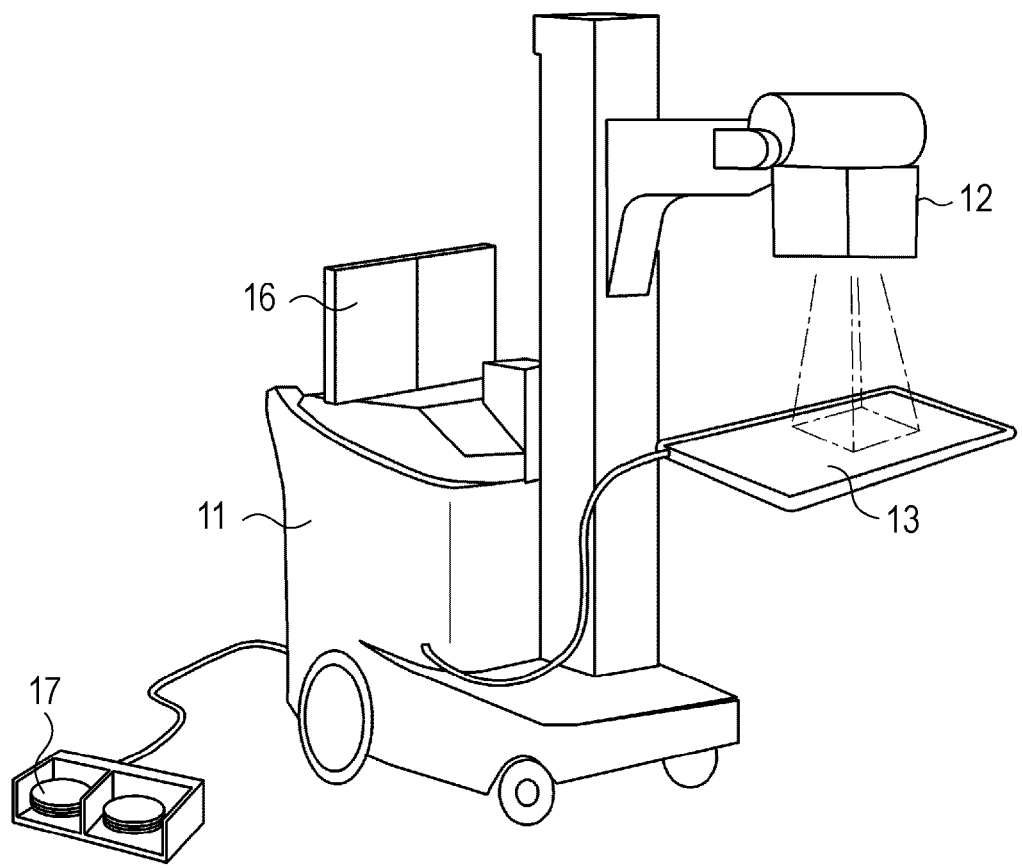
FIG. 16 is a system diagram illustrating an X-ray radiography apparatus according to a fifth embodiment.

FIG. 16 is a system diagram illustrating the structure of an X-ray radiography apparatus according to a fifth embodiment. A movable instrument carriage 11 has an X-ray generating unit 12 including an X-ray source, an X-ray sensor 13 including a flat panel detector, a display unit 16, and a foot pedal 17, and is configured to perform a general X-ray radiographic operation.

The X-ray generating unit 12 has a mechanism including an X-ray tube and an X-ray stop for generating X-rays. The X-ray sensor 13 functions as a detector that receives the X-rays emitted by the X-ray generating unit 12 and obtains image signals. The display unit 16 includes a general monitor, such as a CRT monitor and a liquid crystal display, and displays image data, a graphical user interface (GUI), etc. on a screen. The foot pedal 17 functions as an input device for issuing an instruction to start or stop the emission of the X-rays. The X-ray radiography apparatus also includes a general input device (not shown) including, for example, a keyboard, a mouse, etc., in addition to the foot pedal 17, so that a user can input commands through the input device. In addition, a control device for controlling the X-ray radiography apparatus is disposed in the housing of the instrument carriage 11.

Figure 17:
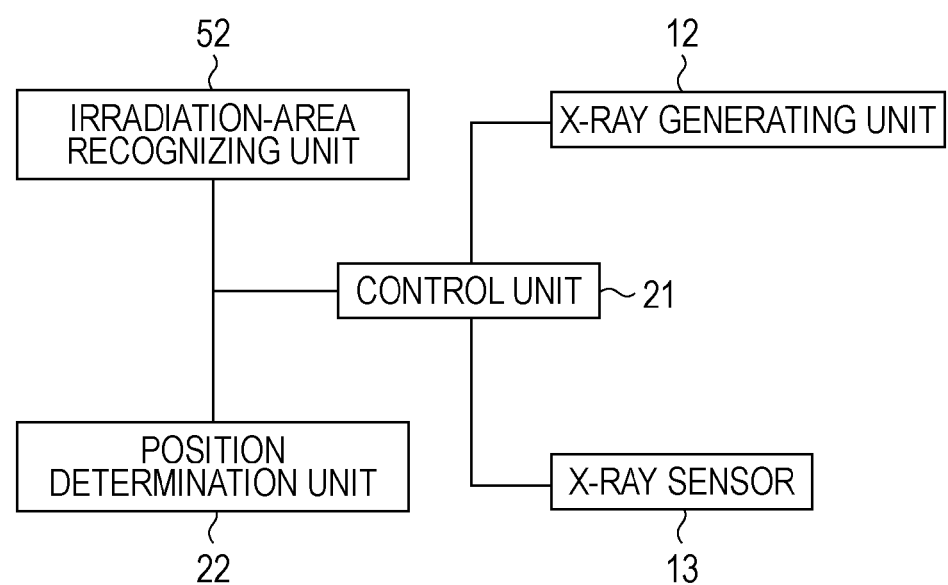
FIG. 17 is a block circuit diagram illustrating the structure of the fifth embodiment.

FIG. 17 is a block circuit diagram of the X-ray radiography apparatus. A control unit 21 is disposed in the housing of the instrument carriage 11, and is connected to the X-ray generating unit 12, the X-ray sensor 13, an irradiation-area recognizing unit 52, and a position determining unit 22. The irradiation-area recognizing unit 52 and the position determining unit 22 are disposed in the housing of the instrument carriage 11 together with the control unit 21. The control unit 21, the irradiation-area recognizing unit 52, and the position determining unit 22 are provided as functions obtained by causing a central processing unit (CPU) (not shown) to execute programs. The CPU may include an LSI or an ASIC.

Figure 18:
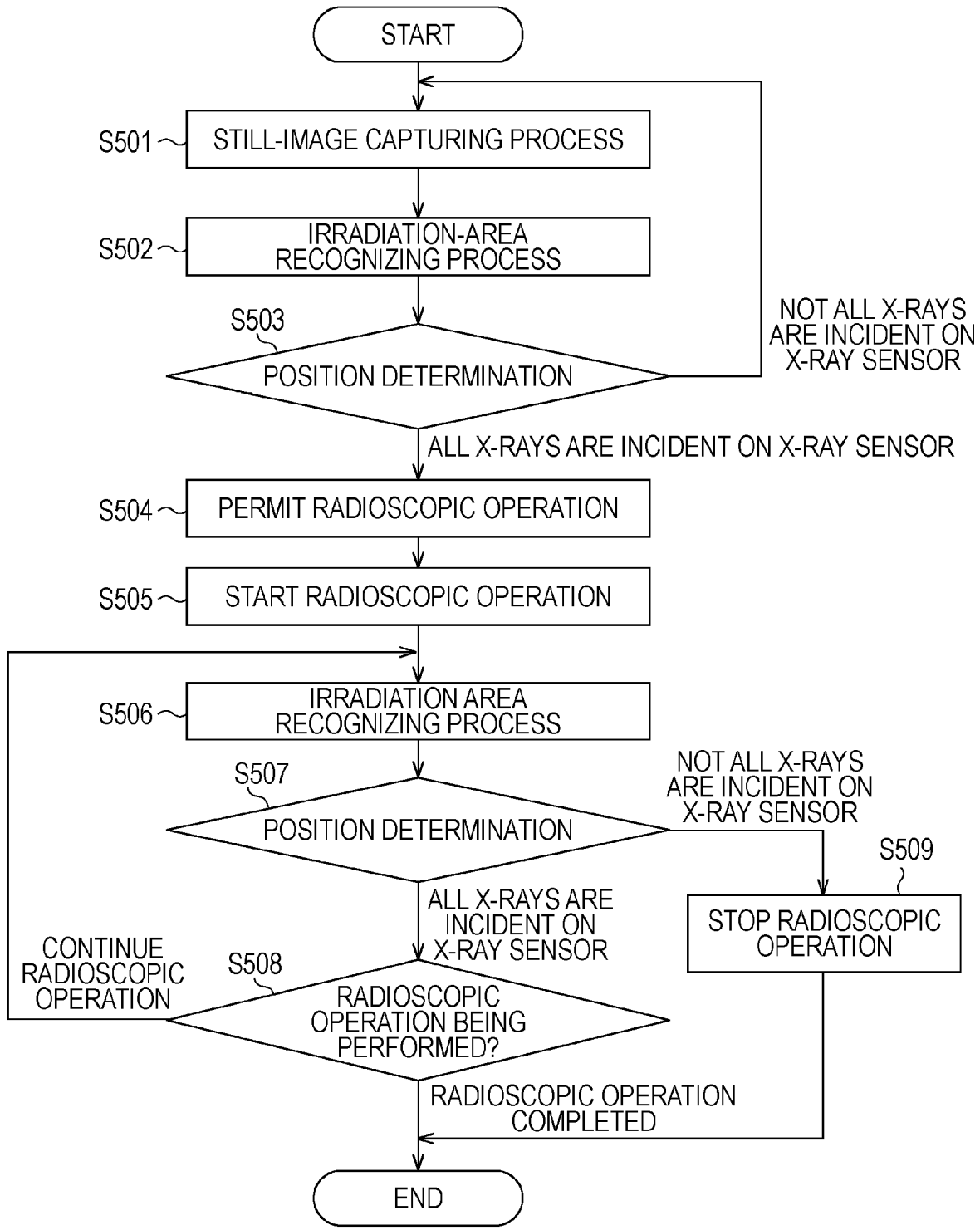
FIG. 18 is a flowchart of the operation according to the fifth embodiment.

FIG. 18 is a flowchart of the operation of the X-ray radiography apparatus. First, in step S501, the control unit 21 is operated so as to perform a still-image capturing operation. In the still-image capturing operation, the X-rays emitted from the X-ray generating unit 12 pass through an object and are incident on the X-ray sensor 13. The X-ray sensor 13 converts the X-rays into electrical signals which are stored as digital data. A still image captured in this process is a single image, and the captured image is not particularly limited as long as the irradiation area can be recognized. Therefore, the conditions of the X-rays may either be set to those for a normal operation for capturing a still image or to those for the radioscopic operation.

Then, an irradiation-area recognizing process is performed in S502 on the basis of the captured still image. The irradiation-area recognizing process is performed by the irradiation-area recognizing unit 52 under the control of the control unit 21. In the irradiation-area recognizing process, the X-ray irradiation area T on the X-ray sensor 13 is determined by performing a known image analyzing process. Thus, the X-ray irradiation area T on the X-ray sensor 13 can be determined by performing the process of recognizing the irradiation area.

In general, the X-ray irradiation area can be varied in accordance with the conditions of the X-ray generating device.

Figure 19:
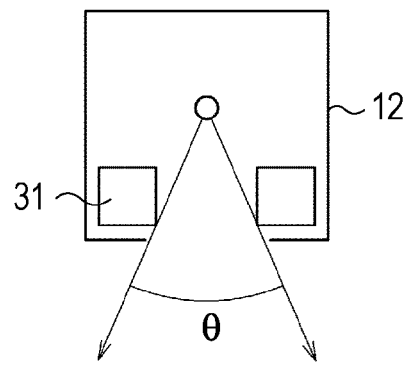
FIG. 19 is a schematic diagram of an X-ray emitting unit according to the fifth embodiment.

FIG. 19 is a schematic diagram of the X-ray generating unit 12 that functions as the X-ray generating device. The X-ray generating unit 12 generally has an opening at the emission side thereof, and an emission angle θ of the X-ray generating unit 12 is generally determined by the opening. More specifically, an X-ray stop 31 is disposed at the opening, and the X-ray irradiation area T can be freely adjusted by adjusting an aperture in the X-ray stop 31 and the position thereof. Therefore, the target angle of the X-rays and the shape of the X-ray irradiation area T can be varied in accordance with the adjustment of the X-ray stop 31. The shape of the X-ray irradiation area T is not limited to rectangular, and may also be hexagonal, octagonal, etc., depending on the shape of the X-ray stop 31.

Next, a position determination process is performed in step S503. The position determination process is performed by the position determining unit 22 under the control of the control unit 21, and it is determined whether or not the X-ray irradiation area T extracted in step S502 is disposed inside the X-ray sensor 13. More specifically, it is determined that the X-ray irradiation area T is disposed inside the X-ray sensor 13 if none of the peripheral sides of the X-ray irradiation area T intersects any of the peripheral sides of the X-ray sensor 13.

Figure 20:
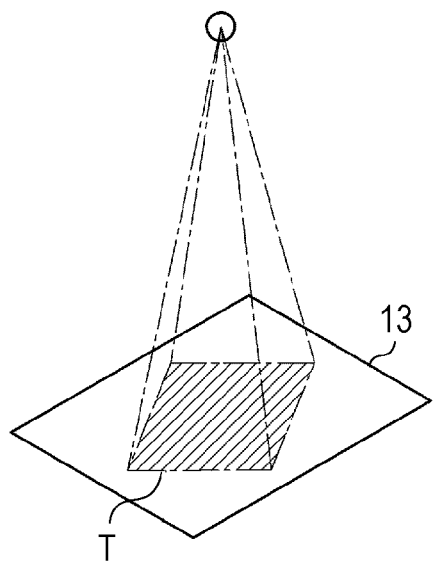
FIG. 20 illustrates the state in which an X-ray irradiation area is disposed inside an X-ray sensor according to the fifth embodiment.

FIG. 20 shows the case in which the X-ray irradiation area T is disposed inside the X-ray sensor 13. None of the peripheral sides of the X-ray irradiation area T intersects any of the peripheral sides of the X-ray sensor 13. If no X-ray is incident on the X-ray sensor 13, the X-ray irradiation area T cannot be recognized by the irradiation-area recognizing unit 52 and an error is issued.

Figure 21:
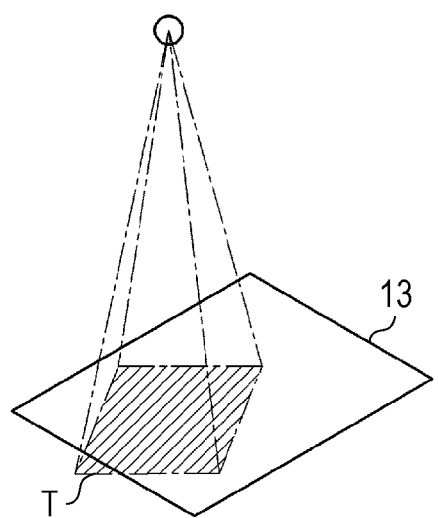
FIG. 21 illustrates the state in which the X-ray irradiation area is not disposed inside the X-ray sensor according to the fifth embodiment.

In comparison, if any of the peripheral sides of the X-ray irradiation area T intersect any of the peripheral sides of the X-ray sensor 13, as shown in FIG. 21, it is determined that the X-ray irradiation area T is not disposed inside the area of the X-ray sensor 13. In FIG. 21, the X-ray sensor 13 and the X-ray irradiation area T overlap each other, and one of the peripheral sides of the X-ray sensor 13 intersects the peripheral sides of the X-ray irradiation area T.

As another method for the position determination process, it may be determined that the X-ray irradiation area T is disposed inside the X-ray sensor 13 if none of the peripheral sides of the X-ray irradiation area T extracted in step S502 coincides with any of the peripheral sides of the X-ray sensor 13. If any of the peripheral sides of the X-ray irradiation area T coincide with any of the peripheral sides of the X-ray sensor 13, it is determined that the X-ray irradiation area T is not disposed inside the X-ray sensor 13.

If it is determined that the X-ray irradiation area T is disposed inside the X-ray sensor 13 as a result of the position determination process, the process proceeds to step S504. If the X-ray irradiation area T protrudes from the X-ray sensor 13, the system returns to the initial state.

Next, in step S504, the X-ray radioscopic operation is permitted by the control unit 21. For example, selection of the radioscopic mode by the user through the GUI can be enabled, or the radioscopic operation can be started when the control unit 21 receives a request to perform the radioscopic operation from an external device.

The X-ray radioscopic operation refers to the operation in which the X-rays are continuously emitted toward the object and the X-rays that pass through the object are converted into electrical signals by the X-ray sensor 13. The electrical signals are continuously displayed on a monitor, so that a moving image can be observed in real time. The radioscopic operation refers to various kinds of continuous image-capturing operations in general, and includes cinematography and digital subtraction angiography (DSA). At the time when the X-ray radioscopic operation is permitted, the X-ray generating unit 12 and the X-ray sensor 13 may be locked to prevent the X-ray generating unit 12 and the X-ray sensor 13 from moving.

Next, in step S505, the X-ray radioscopic operation is started. The radioscopic operation is performed under the control of the control unit 21. The X-rays are continuously emitted by the X-ray generating unit 12 and received by the X-ray sensor 13, and an image is displayed accordingly. Then, the irradiation-area recognizing process is performed in step S506. The irradiation-area recognizing process is performed by the irradiation-area recognizing unit 52 under the control of the control unit 21. The irradiation-area recognizing process performed in step S506 is similar to that performed in step S502. However, a still image is processed in step S502, whereas a single frame of a radiographic image is used to perform the irradiation-area recognizing process in step S506. The image to be subjected to the irradiation-area recognizing process can be changed in accordance with the image-capturing frame rate. For example, the irradiation-area recognizing process may be performed for all of the frames, or be performed once every predetermined time period.

Next, the position determination process is performed in step S507. The position determination process is performed by the position determining unit 22 under the control of the control unit 21. The determination method used in this process is similar to that used in step S503. If it is determined that the X-ray irradiation area T is disposed inside the X-ray sensor 13, the process proceeds to step S508. If it is determined that the X-ray irradiation area T protrudes from the X-ray sensor 13, the process proceeds to step S509. In step S508, it is determined whether or not the X-ray radioscopic operation is being performed. It is determined that the radioscopic operation is being performed when, for example, an instruction to emit radiation is issued from a radiation emission instructing unit, such as the foot pedal 17, or when the X-rays are being emitted by the X-ray generating unit 12. This information is controlled by the control unit 21, and therefore the control unit 21 is capable of determining whether of not the radioscopic operation is being performed. If it is determined that the radioscopic operation is being performed, the process proceeds to step S506. If it is determined that the radioscopic operation is finished, the process is ended.

In step S509, the radioscopic operation is stopped. The process of stopping the radioscopic operation is performed by the control unit 21 by issuing a command to stop the X-ray generating unit 12 from emitting the X-rays. The process of reading the radiographic image by the X-ray sensor 13 is also stopped.

Sixth Embodiment

Figure 22:
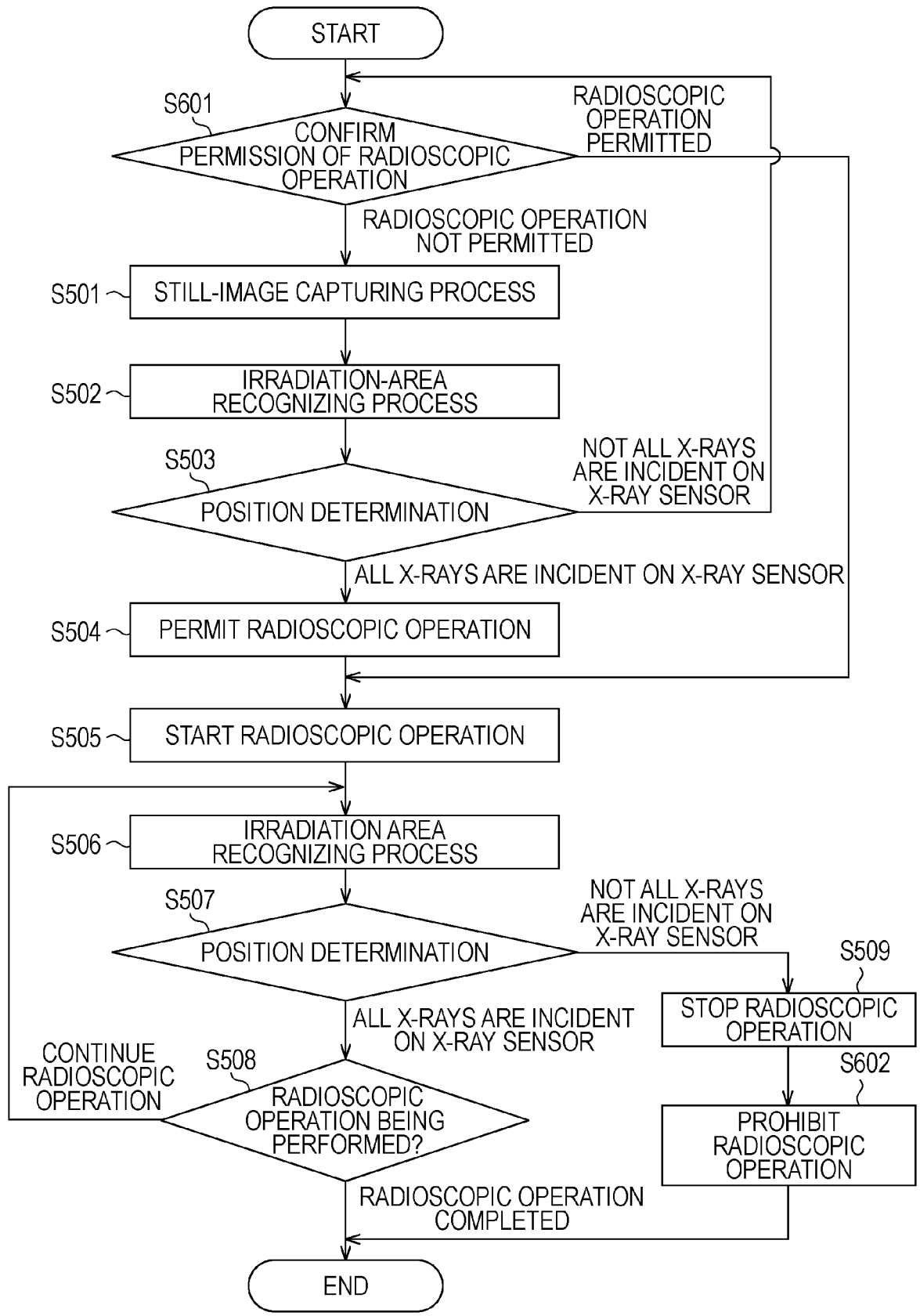
FIG. 22 is a flowchart of the operation according to the sixth embodiment.

FIG. 22 is a flowchart of the operation according to a sixth embodiment. In FIG. 22, steps similar to those of the fifth embodiment shown in FIG. 18 are denoted by the same step numbers. In the sixth embodiment, some of the steps according to the fifth embodiment are repeatedly performed. First, in step S601, it is determined whether or not the X-ray radioscopic operation is permitted. The determination of whether or not the radioscopic operation is permitted is performed by the control unit 21. If the radioscopic operation is permitted, the process proceeds to step S505. If the radioscopic operation is not permitted, the process proceeds to step S501.

Step S506 and the following steps are similar to those of the fifth embodiment. After the radioscopic operation is stopped in step S509, the radioscopic operation is prohibited in step S602 by the control unit 21. For example, selection of the radioscopic mode by the user through the GUI can be disabled, or the control unit 21 may be operated so as not to perform the radioscopic operation even if the control unit 21 receives a request to perform the radioscopic operation from the outside.

Seventh Embodiment

In the position determination process performed in the fifth and sixth embodiments, the peripheral sides of the X-ray sensor 13 and the peripheral sides of the X-ray irradiation area T are used. In the present embodiment, a margin is set along the periphery of the X-ray sensor 13 by setting a certain threshold, and the determination is made using sides disposed slightly inside the X-ray sensor 13.

Figure 23:
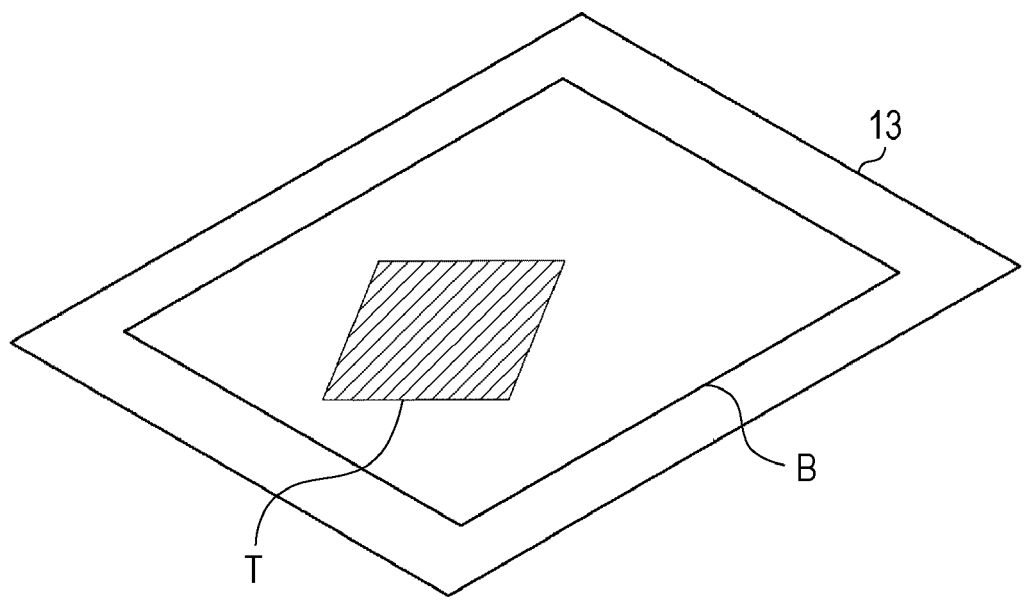
FIG. 23 is a diagram illustrating a rectangle used for position determination according to a seventh embodiment.
Figure 24:
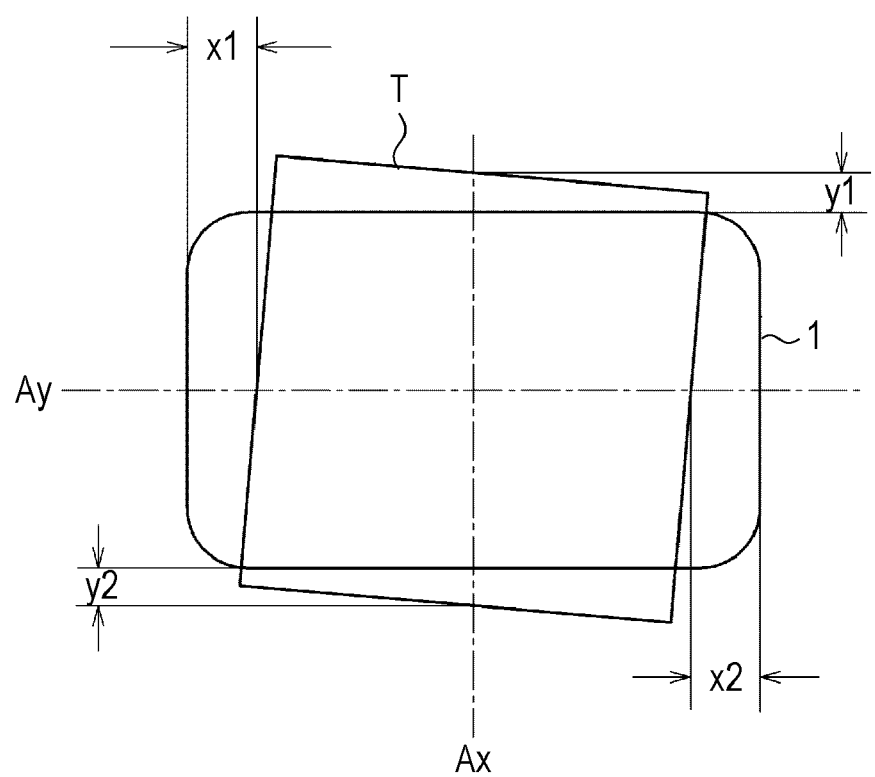
FIG. 24 is a diagram illustrating the state in which an X-ray irradiation area and a sensor surface do not coincide with each other in the known structure.

FIG. 23 is a diagram illustrating the position determination process according to the present embodiment. A rectangular section B disposed inside the X-ray sensor 13 with a predetermined margin along the periphery is used for the position detection process instead of the peripheral sides of the X-ray sensor 13. For example, the rectangular section B is disposed inside the X-ray sensor 13 with a margin of about 1 cm along the periphery of the X-ray sensor 13. The above-described method may be stored in a storage medium, such as a disc, a floppy disk, etc., in the form of a program that can be supplied to the X-ray radiography apparatus.

Although the X-ray radiography apparatus has been described in the first to seventh embodiments, the embodiments of the present invention may also be applied to more general types of radiography apparatuses.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Application No. 2007-163352 filed Jun. 21, 2007 and No. 2007-163353 filed Jun. 21, 2007, which are hereby incorporated by reference herein in their entirety.

What is claimed is:

1. A control device which controls a radiography apparatus including a radiation generating unit that emits radiation and a radiation detecting unit that detects the radiation emitted from the radiation generating unit, the control device comprising:
   a positional-relationship detecting unit that detects a positional relationship between the radiation generating unit and the radiation detecting unit when the radiography apparatus performs a radiographic operation; and
   a control unit that controls the radiographic operation of the radiography apparatus based on the result of the detection performed by the positional-relationship detecting unit.

2. The control device according to claim 1, wherein the positional-relationship detecting unit includes a movement detecting unit configured to detect a movement of at least one of the radiation generating unit and the radiation detecting unit, and
   wherein the control unit controls the radiographic operation of the radiography apparatus based on the result of the detection performed by the movement detecting unit.

3. The control device according to claim 2, wherein the control unit stops the radiographic operation performed by the radiography apparatus when the movement detecting unit detects a movement of at least one of the radiation generating unit and the radiation detecting unit.

4. The control device according to claim 1, wherein the control unit permits the radiography apparatus to perform the radiographic operation when the positional-relationship detecting unit detects that the positional relationship is such that all of the radiation emitted by the radiation generating unit is incident on the radiation detecting unit.

5. The control device according to claim 1, wherein the control unit controls the radiography apparatus to stop the radiographic operation when the positional-relationship detecting unit detects that the positional relationship is such that not all of the radiation emitted by the radiation generating unit is incident on the radiation detecting unit.

6. The control device according to claim 1, wherein the radiation generating unit includes an electromagnetic-wave generator and the radiation detecting unit includes an electromagnetic-wave receiver, and
   wherein the positional-relationship detecting unit detects the positional relationship between the radiation generating unit and the radiation detecting unit based on the state of an electromagnetic wave emitted from the electromagnetic-wave generator and received by the electromagnetic-wave receiver.

7. The control device according to claim 1, wherein at least one of the radiation generating unit and the radiation detecting unit has an inertial sensor, and wherein the positional-relationship detecting unit detects the positional relationship between the radiation generating unit and the radiation detecting unit based on a detection result obtained by the inertial sensor.

8. The control device according to claim 1, wherein the positional-relationship detecting unit includes an irradiation-area recognizing unit configured to recognize an area irradiated with the radiation, and wherein the positional-relationship detecting unit detects the positional relationship between the radiation generating unit and the radiation detecting unit based on a recognition result obtained by the irradiation-area recognizing unit.

9. The control device according to claim 8, wherein the control unit permits the radiography apparatus to perform the radiographic operation when the irradiation area recognized by the irradiation-area recognizing unit is disposed inside the radiation detecting unit.

10. The control device according to claim 8, wherein the control unit controls the radiography apparatus to stop the radiographic operation when the irradiation area recognized by the irradiation-area recognizing unit is not disposed inside the radiation detecting unit.

11. A control device which controls a radiography apparatus including a radiation generating unit that emits radiation and a radiation detecting unit that detects the radiation emitted from the radiation generating unit, the control device comprising:

a positional-relationship detecting unit that detects a positional relationship between the radiation generating unit and the radiation detecting unit when the radiography apparatus performs a radiographic operation; and a control unit that controls the radiographic operation of the radiography apparatus based on the positional relationship detected by the positional-relationship detecting unit.

* * * * *